(12) United States Patent
Elomari

(10) Patent No.: US 9,056,311 B2
(45) Date of Patent: Jun. 16, 2015

(54) METHOD FOR MAKING MOLECULAR SIEVE SSZ-96

(71) Applicant: Saleh Ali Elomari, Fairfield, CA (US)

(72) Inventor: Saleh Ali Elomari, Fairfield, CA (US)

(73) Assignee: CHEVRON U.S.A. INC., San Ramon, CA (US)

( * ) Notice: Subject to any disclaimer, the term of this patent is extended or adjusted under 35 U.S.C. 154(b) by 146 days.

(21) Appl. No.: 14/052,235

(22) Filed: Oct. 11, 2013

(65) Prior Publication Data
US 2015/0104377 A1    Apr. 16, 2015

(51) Int. Cl.
| | |
|---|---|
| C01B 33/36 | (2006.01) |
| C01B 39/00 | (2006.01) |
| B01J 29/85 | (2006.01) |
| C01B 39/48 | (2006.01) |
| B01J 29/70 | (2006.01) |
| C07C 2/12 | (2006.01) |
| C01B 37/02 | (2006.01) |

(52) U.S. Cl.
CPC ............... *B01J 29/85* (2013.01); *C01B 39/48* (2013.01); *B01J 29/70* (2013.01); *C07C 2/12* (2013.01); *C01B 37/02* (2013.01)

(58) Field of Classification Search
CPC ........ C01B 37/02; C01B 39/48; C01B 39/04; B01J 29/04; B01J 29/07; B01J 29/70; B01J 29/85; C07C 2/12
USPC .................................................. 423/702, 704
See application file for complete search history.

(56) References Cited

U.S. PATENT DOCUMENTS 7,309,558 B1    12/2007    Michel et al.
8,545,801 B1    10/2013    Zones

OTHER PUBLICATIONS

PCT International Search Report, PCT/US2014/038984, mailed Sep. 3, 2014.

*Primary Examiner* — Bijay Saha
(74) *Attorney, Agent, or Firm* — Terrence Flaherty

(57) ABSTRACT

A method for making a new crystalline molecular sieve designated SSZ-96 is disclosed using a 1-butyl-1-methyl-octahydroindolium cation as a structure directing agent.

8 Claims, 2 Drawing Sheets

METHOD FOR MAKING MOLECULAR SIEVE SSZ-96

TECHNICAL FIELD

The present disclosure relates to new crystalline molecular sieve SSZ-96, a method for preparing SSZ-96 using a 1-butyl-1-methyl-octahydroindolium cation as a structure directing agent ("SDA") and uses for SSZ-96.

BACKGROUND

Because of their unique sieving characteristics, as well as their catalytic properties, crystalline molecular sieves and zeolites are especially useful in applications such as hydrocarbon conversion, gas drying and separation. Although many different crystalline molecular sieves have been disclosed, there is a continuing need for new molecular sieves with desirable properties for gas separation and drying, hydrocarbon and chemical conversions, and other applications. New molecular sieves may contain novel internal pore architectures, providing enhanced selectivities in these processes.

SUMMARY

The present disclosure is directed to a family of crystalline molecular sieves with unique properties, referred to herein as "molecular sieve SSZ-96" or simply "SSZ-96."

In one aspect, there is provided a molecular sieve having a mole ratio of at least 10 of (1) at least one oxide of at least one tetravalent element to (2) optionally, one or more oxides selected from the group consisting of oxides of trivalent elements, pentavalent elements, and mixtures thereof, and having, in its calcined form, the X-ray diffraction lines of Table 6. It should be noted that the phrase "mole ratio of at least 10" includes the case where there is no oxide (2), i.e., the mole ratio of oxide (1) to oxide (2) is infinity. In that case, the molecular sieve is comprised of essentially all of the oxide of the one or more tetravalent elements.

In another aspect, there is provided a method of preparing a crystalline molecular sieve by contacting under crystallization conditions (1) at least one source of an oxide of at least one tetravalent element; (2) optionally, one or more sources of one or more oxides selected from the group consisting of oxides of trivalent elements, pentavalent elements, and mixtures thereof; (3) at least one source of an element selected from Groups 1 and 2 of the Periodic Table; (4) hydroxide ions; and (5) a 1-butyl-1-methyl-octahydroindolium cation.

In yet another aspect, there is provided a process for preparing a crystalline molecular sieve having, in its calcined form, the X-ray diffraction lines of Table 6, by: (a) preparing a reaction mixture containing (1) at least one source of an oxide of at least one tetravalent element; (2) optionally, one or more sources of one or more oxides selected from the group consisting of oxides of trivalent elements, pentavalent elements, and mixtures thereof; (3) at least one source of an element selected from Groups 1 and 2 of the Periodic Table; (4) hydroxide ions; (5) a 1-butyl-1-methyl-octahydroindolium cation, and (6) water; and (b) maintaining the reaction mixture under crystallization conditions sufficient to form crystals of the molecular sieve.

The present disclosure also provides SSZ-96 molecular sieves having a composition, as-synthesized and in the anhydrous state, in terms of mole ratios, as follows:

| | Broad | Exemplary |
|---|---|---|
| $TO_2/X_2O_n$ | ≥10 | 20 to 100 |
| $Q/TO_2$ | 0.05 to 0.5 | 0.1 to 0.3 |
| $M/TO_2$ | 0.01 to 0.6 | 0.02 to 0.35 | wherein: (1) T is selected from the group consisting of tetravalent elements from Groups 4-14 of the Periodic Table, and mixtures thereof; (2) X is selected from the group consisting of trivalent and pentavalent elements from Groups 3-13 of the Periodic Table, and mixtures thereof; (3) stoichiometric variable n equals the valence state of compositional variable X (e.g., when X is trivalent, n=3; when X is pentavalent, n=5); (4) Q is a 1-butyl-1-methyl-octahydroindolium cation; and (5) M is selected from the group consisting of elements from Groups 1 and 2 of the Periodic Table.

DETAILED DESCRIPTION

Introduction

Figure 1:
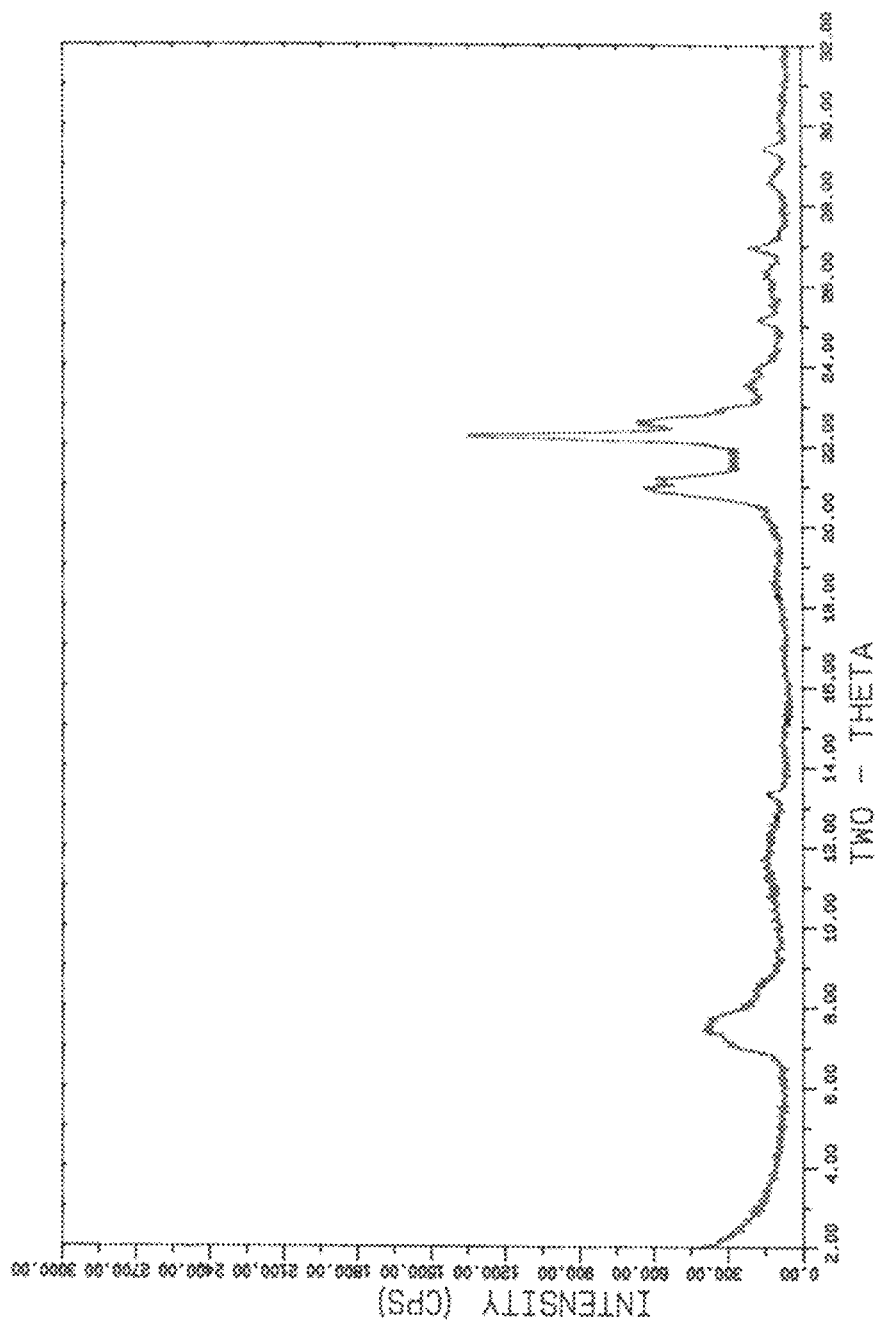
FIG. 1 is a powder X-ray diffraction (XRD) pattern of the as-synthesized molecular sieve prepared in Example 2.

The following terms will be used throughout the specification and will have the following meanings unless otherwise indicated.

The term "active source" means a reagent or precursor material capable of supplying at least one element in a form that can react and which can be incorporated into the molecular sieve structure. The terms "source" and "active source" can be used interchangeably herein.

The term "Periodic Table" refers to the version of IUPAC Periodic Table of the Elements dated Jun. 22, 2007, and the numbering scheme for the Periodic Table Groups is as described in Chem. Eng. News, 63(5), 26-27 (1985).

In preparing SSZ-96, a 1-butyl-1-methyl-octahydroindolium cation is used as a structure directing agent ("SDA"), also known as a crystallization template. The SDA useful for making SSZ-96 is represented by the following structure (1):

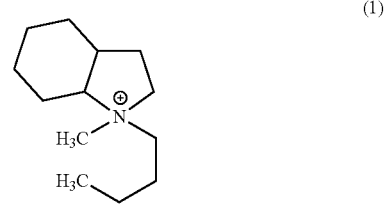

(1)

The SDA cation is associated with anions which can be any anion that is not detrimental to the formation of SSZ-96. Representative anions include elements from Group 17 of the Periodic Table (e.g., fluoride, chloride, bromide and iodide), hydroxide, acetate, sulfate, tetrafluoroborate, carboxylate, and the like.

Reaction Mixture

In general, SSZ-96 is prepared by: (a) preparing a reaction mixture containing (1) at least one source of an oxide of at least one tetravalent element; (2) optionally, one or more sources of one or more oxides selected from the group consisting of oxides of trivalent elements, pentavalent elements, and mixtures thereof; (3) at least one source of an element selected from Groups 1 and 2 of the Periodic Table; (4) hydroxide ions; (5) a 1-butyl-1-methyl-octahydroindolium cation; and (6) water; and (b) maintaining the reaction mixture under crystallization conditions sufficient to form crystals of the molecular sieve.

The composition of the reaction mixture from which the molecular sieve is formed, in terms of mole ratios, is identified in Table 1 below, wherein compositional variables T, X, M, and Q and stoichiometric variable n are as described herein above.

TABLE 1

| Components | Broad | Exemplary |
|---|---|---|
| $TO_2/X_2O_n$ | ≥10 | 20 to 100 |
| $M/TO_2$ | 0.01 to 1.0 | 0.02 to 0.35 |
| $Q/TO_2$ | 0.05 to 0.5 | 0.1 to 0.3 |
| $OH/TO_2$ | 0.1 to 1.0 | 0.2 to 0.6 |
| $H_2O/TO_2$ | 10 to 100 | 20 to 50 |

In one sub-embodiment, the composition of the reaction mixture from which SSZ-96 is formed, in terms of mole ratios, is identified in Table 2 below, wherein compositional variables M and Q are as described herein above.

TABLE 2

| Components | Broad | Exemplary |
|---|---|---|
| $SiO_2/Al_2O_3$ | ≥10 | 20 to 100 |
| $M/SiO_2$ | 0.01 to 1.0 | 0.02 to 0.35 |
| $Q/SiO_2$ | 0.05 to 0.5 | 0.1 to 0.3 |
| $OH/SiO_2$ | 0.1 to 1.0 | 0.2 to 0.6 |
| $H_2O/SiO_2$ | 10 to 100 | 20 to 50 |

As noted above, for each embodiment described herein, T is selected from the group consisting of tetravalent elements from Groups 4-14 of the Periodic Table. In one sub-embodiment, T is selected from the group consisting of silicon (Si), germanium (Ge), titanium (Ti), and mixtures thereof. In another sub-embodiment, T is selected from the group consisting of Si, Ge, and mixtures thereof. In one sub-embodiment, T is Si. Sources of elements selected for composition variable T include oxides, hydroxides, acetates, oxalates, ammonium salts and sulfates of the element(s) selected for T. In one sub-embodiment, each source(s) of the element(s) selected for composition variable T is an oxide. Where T is Si, sources useful for Si include fumed silica, precipitated silicates, silica hydrogel, silicic acid, colloidal silica, tetra-alkyl orthosilicates (e.g., tetraethyl orthosilicate), and silica hydroxides. Sources useful herein for Ge include germanium oxide and germanium ethoxide.

For each embodiment described herein, X is selected from the group consisting of elements from Groups 3-13 of the Periodic Table. In one sub-embodiment, X is selected from the group consisting of boron (B), aluminum (Al), gallium (Ga), indium (In), iron (Fe), and mixtures thereof. In another sub-embodiment, X is selected from the group consisting of B, Al, Ga, In, and mixtures thereof. In one sub-embodiment X is Al. Sources of elements selected for optional composition variable X include oxides, hydroxides, acetates, oxalates, ammonium salts and sulfates of the element(s) selected for X. Where X is Al, sources useful for Al include aluminates, alumina, and aluminum compounds such as $AlCl_3$, $Al_2(SO_4)_3$, $Al(OH)_3$, kaolin clays, and other zeolites. An example of the source of aluminum oxide is LZ-210 zeolite (a type of Y zeolite). Boron, gallium, and iron can be added in forms corresponding to their aluminum and silicon counterparts.

As described herein above, for each embodiment described herein, the reaction mixture can be formed using at least one source of an element selected from Groups 1 and 2 of the Periodic Table (referred to herein as M). In one sub-embodiment, the reaction mixture is formed using a source of an element from Group 1 of the Periodic Table. In another sub-embodiment, the reaction mixture is formed using a source of sodium (Na). Any M-containing compound which is not detrimental to the crystallization process is suitable. Sources for such Groups 1 and 2 elements include oxides, hydroxides, nitrates, sulfates, halides, oxalates, citrates and acetates thereof.

For each embodiment described herein, the molecular sieve reaction mixture can be supplied by more than one source. Also, two or more reaction components can be provided by one source.

The reaction mixture can be prepared either batch wise or continuously. Crystal size, morphology and crystallization time of the molecular sieve described herein can vary with the nature of the reaction mixture and the crystallization conditions.

Crystallization and Post-Synthesis Treatment

In practice, the molecular sieve is prepared by: (a) preparing a reaction mixture as described herein above; and (b) maintaining the reaction mixture under crystallization conditions sufficient to form crystals of the molecular sieve.

The reaction mixture is maintained at an elevated temperature until the crystals of the molecular sieve are formed. The hydrothermal crystallization is usually conducted under pressure, and usually in an autoclave so that the reaction mixture is subject to autogenous pressure, at a temperature between 125° C. and 200° C.

The reaction mixture can be subjected to mild stirring or agitation during the crystallization step. It will be understood by one skilled in the art that the molecular sieves described herein can contain impurities, such as amorphous materials, unit cells having framework topologies which do not coincide with the molecular sieve, and/or other impurities (e.g., organic hydrocarbons).

During the hydrothermal crystallization step, the molecular sieve crystals can be allowed to nucleate spontaneously from the reaction mixture. The use of crystals of the molecular sieve as seed material can be advantageous in decreasing the time necessary for complete crystallization to occur. In addition, seeding can lead to an increased purity of the product obtained by promoting the nucleation and/or formation of the molecular sieve over any undesired phases. When used as seeds, seed crystals are added in an amount between 1% and 10% of the weight of the source for compositional variable T used in the reaction mixture.

Once the molecular sieve crystals have formed, the solid product is separated from the reaction mixture by standard mechanical separation techniques such as filtration. The crystals are water-washed and then dried to obtain the as-synthesized molecular sieve crystals. The drying step can be performed at atmospheric pressure or under vacuum.

The molecular sieve can be used as-synthesized, but typically will be thermally treated (calcined). The term "as-synthesized" refers to the molecular sieve in its form after crystallization, prior to removal of the SDA cation. The SDA can be removed by thermal treatment (e.g., calcination), preferably in an oxidative atmosphere (e.g., air, gas with an oxygen partial pressure of greater than 0 kPa) at a temperature readily determinable by one skilled in the art sufficient to remove the SDA from the molecular sieve. The SDA can also be removed by photolysis techniques (e.g., exposing the SDA-containing molecular sieve product to light or electromagnetic radiation that has a wavelength shorter than visible light under conditions sufficient to selectively remove the organic compound from the molecular sieve) as described in U.S. Pat. No. 6,960,327.

The molecular sieve can subsequently be calcined in steam, air or inert gas at temperatures ranging from 200° C. to 800° C. for periods of time ranging from 1 to 48 hours, or more. Usually, it is desirable to remove the extra-framework cation (e.g., $Na^+$) by ion exchange and replace it with hydrogen, ammonium, or any desired metal-ion.

Where the molecular sieve formed is an intermediate molecular sieve, the target molecular sieve can be achieved using post-synthesis techniques such as heteroatom lattice substitution techniques. The target molecular sieve (e.g., silicate SSZ-96) can also be achieved by removing heteroatoms from the lattice by known techniques such as acid leaching.

The molecular sieve made from the process disclosed herein can be formed into a wide variety of physical shapes. Generally speaking, the molecular sieve can be in the form of a powder, a granule, or a molded product, such as extrudate having a particle size sufficient to pass through a 2-mesh (Tyler) screen and be retained on a 400-mesh (Tyler) screen. In cases where the catalyst is molded, such as by extrusion with an organic binder, the molecular sieve can be extruded before drying or dried (or partially dried) and then extruded.

The molecular sieve can be composited with other materials resistant to the temperatures and other conditions employed in organic conversion processes. Such matrix materials include active and inactive materials and synthetic or naturally occurring zeolites as well as inorganic materials such as clays, silica and metal oxides. Examples of such materials and the manner in which they can be used are disclosed in U.S. Pat. Nos. 4,910,006 and 5,316,753.

SSZ-96 is useful in catalysts for a variety of hydrocarbon conversion reactions such as hydrocracking, dewaxing, olefin isomerization, alkylation of aromatic compounds and the like. SSZ-96 is also useful as an adsorbent for separations.

Characterization of the Molecular Sieve

Molecular sieves made by the process disclosed herein have a composition, as-synthesized and in the anhydrous state, as described in Table 3 (in terms of mole ratios), wherein compositional variables T, X, Q and M and stoichiometric variable n are as described herein above:

TABLE 3

|  | Broad | Exemplary |
|---|---|---|
| $TO_2/X_2O_n$ | ≥10 | 20 to 100 |
| $Q/TO_2$ | 0.05 to 0.5 | 0.1 to 0.3 |
| $M/TO_2$ | 0.01 to 0.6 | 0.02 to 0.35 |

In one sub-embodiment, the molecular sieves made by the process disclosed herein have a composition, as-synthesized and in the anhydrous state, as described in Table 4 (in terms of mole ratios), wherein compositional variables Q and M are as described herein above:

TABLE 4

|  | Broad | Exemplary |
|---|---|---|
| $SiO_2/Al_2O_3$ | ≥10 | 20 to 100 |
| $Q/SiO_2$ | 0.05 to 0.5 | 0.1 to 0.3 |
| $M/SiO_2$ | 0.01 to 0.6 | 0.02 to 0.35 |

Molecular sieves synthesized by the process disclosed herein can be characterized by their XRD pattern. The powder XRD lines of Table 5 are representative of as-synthesized SSZ-96 made in accordance with the method described herein. Minor variations in the diffraction pattern can result from variations in the mole ratios of the framework species of the particular sample due to changes in lattice constants. In addition, sufficiently small crystals will affect the shape and intensity of peaks, leading to significant peak broadening. Minor variations in the diffraction pattern can also result from variations in the organic compound used in the preparation. Calcination can also cause minor shifts in the XRD pattern. Notwithstanding these minor perturbations, the basic crystal lattice structure remains unchanged.

TABLE 5

Characteristic Peaks for As-Synthesized SSZ-96

| 2-Theta[a] | d-spacing (nm) | Relative Intensity[b] |
|---|---|---|
| 7.60 | 1.162 | S |
| 8.47 | 1.043 | W |
| 21.00 | 0.423 | S |
| 22.28 | 0.399 | VS |
| 22.66 | 0.392 | VS |
| 23.64 | 0.376 | W |
| 25.20 | 0.353 | W |
| 26.94 | 0.331 | W |
| 28.60 | 0.312 | W |
| 29.48 | 0.303 | W |
| 33.20 | 0.270 | W |
| 37.80 | 0.238 | W |

[a] ±0.20
[b] The powder XRD patterns provided are based on a relative intensity scale in which the strongest line in the X-ray pattern is assigned a value of 100: W = weak (>0 to ≤20); M = medium (>20 to ≤40); S = strong (>40 to ≤60); VS = very strong (>60 to ≤100).

The X-ray diffraction pattern lines of Table 6 are representative of calcined SSZ-96 made in accordance with the method described herein.

TABLE 6

Characteristic Peaks for Calcined SSZ-96

| 2-Theta[a] | d-spacing (nm) | Relative Intensity[b] |
|---|---|---|
| 7.50 | 1.178 | VS |
| 8.52 | 1.037 | M |
| 14.50 | 0.610 | W |
| 20.86 | 0.425 | S |
| 22.26 | 0.399 | VS |
| 22.76 | 0.390 | S |
| 23.60 | 0.377 | W |
| 24.02 | 0.370 | W |
| 25.16 | 0.354 | W |
| 26.40 | 0.337 | W |
| 26.94 | 0.331 | W |
| 28.57 | 0.312 | W |
| 29.41 | 0.303 | W |

[a] ±0.20
[b] The powder XRD patterns provided are based on a relative intensity scale in which the strongest line in the X-ray pattern is assigned a value of 100: W = weak (>0 to ≤20); M = medium (>20 to ≤40); S = strong (>40 to ≤60); VS = very strong (>60 to ≤100).

The powder X-ray diffraction patterns presented herein were collected by standard techniques. The radiation was $CuK_\alpha$ radiation. The peak heights and the positions, as a function of 2θ where θ is the Bragg angle, were read from the relative intensities of the peaks (adjusting for background), and d, the interplanar spacing corresponding to the recorded lines, can be calculated.

EXAMPLES

The following illustrative examples are intended to be non-limiting.

Example 1

Synthesis of 1-butyl-1-methyl-octahydroindolium cation

Synthesis of 1-methyl-octahydroindole

To a solution of 100 g of 1-methylindole in absolute ethanol in a 600 mL autoclave, 5 g of $PtO_2$ and 10 mL of $H_2SO_4$ were added. The mixture was sealed and pressurized with hydrogen to 1500 psig. The reaction mixture was heated at 100° C. overnight while stirring at about 400 rpm. The reaction mixture was pressurized again to 1500 psig and heated at 100° C. for several more hours. The reaction mixture was cooled and filtered to remove the catalyst. The filtrate was concentrated on a rotary evaporator to remove ethanol. The residue was neutralized with sodium hydroxide solution and left to stir at room temperature for about 30 minutes. The solution was transferred to a reparatory funnel and extracted with diethyl ether. The ether layer was dried over anhydrous $MgSO_4$, filtered and concentrated at reduced pressure on a rotary evaporator to give 93.0 g of the product, 1-methyl-octahydroindole, as a yellow oil. The product was confirmed by NMR.

Synthesis of 1-butyl-1-methyl-octahydroindolium hydroxide 20 g (0.14 mmol) of 1-methyl-octahydroindole was mixed with 53 g (0.29 mmol) of 1-iodobutane in 300 mL of methanol. The reaction mixture was heated at reflux for 72 hours. Then, an additional 0.5 mol equivalent of 1-iodobutane was added and the reaction mixture was heated for an additional 12 hours. The reaction mixture was cooled and the solvent removed on a rotary evaporator to give an off-white powder which was used without further purification. The quaternization afforded 39.4 g (86% yield) of 1-butyl-1-methyl-octahydroindolium iodide. The obtained 1-butyl-1-methyl-octahydroindolium iodide (18.15 g) was dissolved in 56 g of deionized water. To this solution, 70 g of BIO-RAD AG® 1-X8 ion exchange resin was added and the slurry was gently stirred at room temperature overnight. The solution was filtered and the filtrate analyzed for hydroxide content by titration of a small aliquot with dilute HCl. The exchange afforded 1-butyl-1-methyl-octahydroindolium hydroxide in 87% yield.

Scheme 1 below depicts the synthesis of the SDA.

SCHEME 1

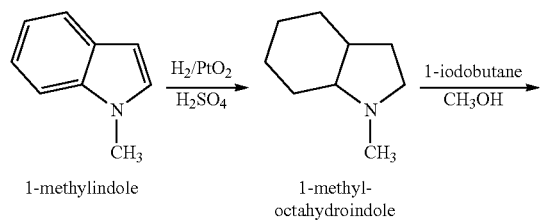

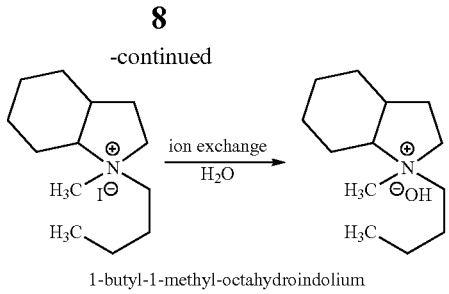

Example 2

Synthesis of SSZ-96

A 23 mL Teflon liner was charged with 4.9 g of 1-butyl-1-methyl-octahydroindolium hydroxide solution (3 mmol of cation and 3 mmol of hydroxide), 0.75 g of 1N NaOH solution, 0.75 g of CAB-O-SIL® M-5 fumed silica (Cabot Corporation), 0.25 g of LZ-210 zeolite and 2 g of deionized water. The resulting gel mixture was stirred thoroughly until a homogeneous solution was obtained. The Teflon liner containing the resulting gel mixture was capped off and placed in a stainless steel Parr autoclave. The autoclave was affixed onto a spit rotating at 43 rpm in an oven at 170° C. The gel mixture was heated for 6 days after which the reaction was completed to give a settled powder and a clear solution. The reaction mixture was filtered and washed thoroughly with deionized water. The solids were dried in air overnight and then dried in an oven at 120° C. for 2 hours. The obtained solids (0.9 g) were analyzed by powder XRD. The powder XRD pattern of the resulting product is shown in FIG. 1 and indicates that the material was unique.

Example 3

Calcination of SSZ-96

Figure 2:
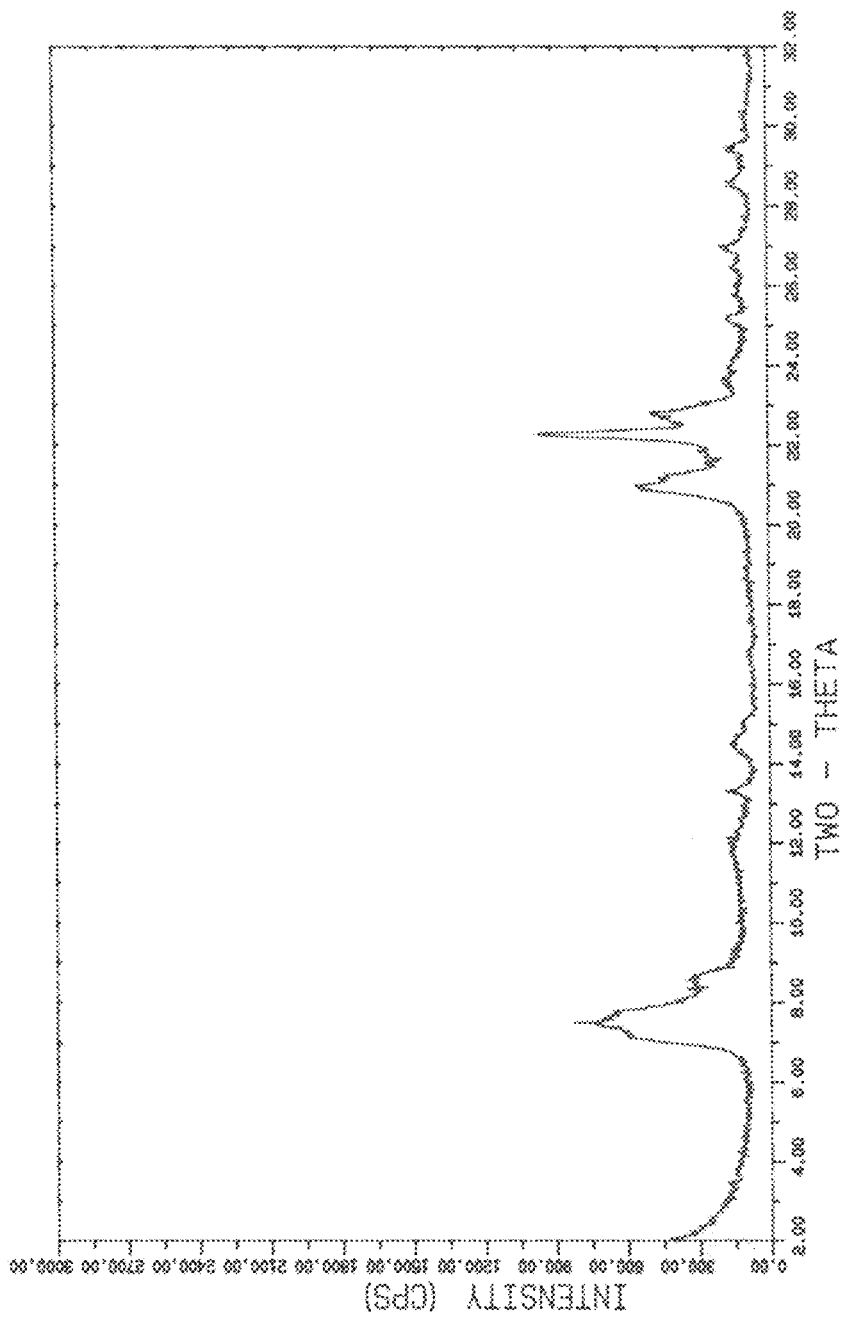
FIG. 2 is a powder XRD pattern of the calcined molecular sieve prepared in Example 3.

The as-synthesized product from Example 2 was calcined in air in a muffle furnace from room temperature to 120° C. at a rate of 1° C./minute and held at 120° C. for 2 hours. The temperature was then ramped up to 540° C. at a rate of 1° C./minute and held at 540° C. for 5 hours. The temperature was then increased at the same rate (1° C./min) to 595° C. at held at 595° C. for 5 hours. The powder XRD pattern of the calcined molecular sieve is shown in FIG. 2 and indicates that the material remains stable after calcination to remove the organic SDA.

The micropore volume and external surface area of calcined SSZ-96 were then measured by nitrogen physisorption using the BET method. The measured micropore volume was 0.13 cm³/g, the external surface area was 59.7 m²/g and the BET surface area was 330.7 m²/g.

For the purposes of this specification and appended claims, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that can vary depending upon the desired properties sought to be obtained. It is noted that, as used in this specification and the appended claims, the singular forms "a," "an," and "the," include plural references unless expressly and unequivocally limited to one referent. As used herein, the term "include" and its grammatical variants are intended to be non-limiting, such that recitation of items in a list is not to the exclusion of other like items that can be substituted or added to the listed items. As used herein, the term "comprising" means including elements or steps that are identified following that term, but any such elements or steps are not exhaustive, and an embodiment can include other elements or steps.

Unless otherwise specified, the recitation of a genus of elements, materials or other components, from which an individual component or mixture of components can be selected, is intended to include all possible sub-generic combinations of the listed components and mixtures thereof.

The patentable scope is defined by the claims, and can include other examples that occur to those skilled in the art. Such other examples are intended to be within the scope of the claims if they have structural elements that do not differ from the literal language of the claims, or if they include equivalent structural elements with insubstantial differences from the literal languages of the claims. To an extent not inconsistent herewith, all citations referred to herein are hereby incorporated by reference.

The invention claimed is:

1. A method for synthesizing a molecular sieve SSZ-96 comprising contacting under crystallization conditions: (1) at least one source of an oxide of at least one tetravalent element; (2) optionally, one or more sources of one or more oxides selected from the group consisting of oxides of trivalent elements, pentavalent elements, and mixtures thereof; (3) at least one source of an element selected from Groups 1 and 2 of the Periodic Table; (4) hydroxide ions; and (5) a 1-butyl-1-methyl-octahydroindolium cation.

2. The method of claim 1, wherein the molecular sieve SSZ-96 is prepared from a reaction mixture comprising, in terms of mole ratios, the following:

| | |
|---|---|
| $TO_2/X_2O_n$ | ≥10 |
| $M/TO_2$ | 0.01 to 1.0 |
| $Q/TO_2$ | 0.05 to 0.5 |
| $OH^-/TO_2$ | 0.1 to 1.0 |
| $H_2O/TO_2$ | 10 to 100 | wherein:
(1) T is selected from the group consisting of tetravalent elements from Groups 4-14 of the Periodic Table, and mixtures thereof;
(2) X is selected from the group consisting of trivalent and pentavalent elements from Groups 3-13 of the Periodic Table, and mixtures thereof;
(3) n equals the valence state of X;
(4) M is selected from the group consisting of elements from Groups 1 and 2 of the Periodic Table; and
(5) Q is a 1-butyl-1-methyl-octahydroindolium cation.

3. The method of claim 2, wherein T is selected from the group consisting of Si, Ge, and mixtures thereof.

4. The method of claim 2, wherein X is selected from the group consisting of B, Al, Ga, In, and mixtures thereof.

5. The method of claim 2, wherein T is Si and X is Al.

6. The method of claim 2, wherein the molecular sieve SSZ-96 is prepared from a reaction mixture comprising, in terms of mole ratios, the following:

| | |
|---|---|
| $TO_2/X_2O_n$ | 20 to 100 |
| $M/TO_2$ | 0.02 to 0.35 |
| $Q/TO_2$ | 0.1 to 0.3 |
| $OH^-/TO_2$ | 0.2 to 0.6 |
| $H_2O/TO_2$ | 20 to 50. |

7. The method of claim 1, wherein the molecular sieve SSZ-96 has, in its calcined form, an X-ray diffraction pattern substantially as shown in the following Table:

| 2-Theta | d-spacing (nm) | Relative Intensity |
|---|---|---|
| 7.50 ± 0.20 | 1.178 | VS |
| 8.52 ± 0.20 | 1.037 | M |
| 14.50 ± 0.20 | 0.610 | W |
| 20.86 ± 0.20 | 0.425 | S |
| 22.26 ± 0.20 | 0.399 | VS |
| 22.76 ± 0.20 | 0.390 | S |
| 23.60 ± 0.20 | 0.377 | W |
| 24.02 ± 0.20 | 0.370 | W |
| 25.16 ± 0.20 | 0.354 | W |
| 26.40 ± 0.20 | 0.337 | W |
| 26.94 ± 0.20 | 0.331 | W |
| 28.57 ± 0.20 | 0.312 | W |
| 29.41 ± 0.20 | 0.303 | W. |

8. The method of claim 1, wherein the molecular sieve SSZ-96 has a composition, as-synthesized and in its anhydrous state, in terms of mole ratios, as follows:

| | |
|---|---|
| $TO_2/X_2O_n$ | ≥10 |
| $Q/TO_2$ | 0.05 to 0.5 |
| $M/TO_2$ | 0.01 to 0.6 | wherein:
(1) T is selected from the group consisting of tetravalent elements from Groups 4-14 of the Periodic Table, and mixtures thereof;
(2) X is selected from the group consisting of trivalent and pentavalent elements from Groups 3-13 of the Periodic Table, and mixtures thereof;
(3) n equals the valence state of X;
(4) Q is a 1-butyl-1-methyl-octahydroindolium cation; and
(5) M is selected from the group consisting of elements from Groups 1 and 2 of the Periodic Table.

* * * * *